United States Patent
Som et al.

(10) Patent No.: US 9,765,287 B2
(45) Date of Patent: Sep. 19, 2017

(54) STABILIZED HYDROGEN PEROXIDE COMPOSITIONS AND METHOD OF MAKING SAME

(71) Applicant: Metrex Research, LLC, Orange, CA (US)

(72) Inventors: Abhigyan Som, Brea, CA (US); Harish Jani, Lake Forest, CA (US)

(73) Assignee: Metrex Research Corporation, Orange, CA (US)

( * ) Notice: Subject to any disclaimer, the term of this patent is extended or adjusted under 35 U.S.C. 154(b) by 0 days.

(21) Appl. No.: 14/729,802

(22) Filed: Jun. 3, 2015

(65) Prior Publication Data

US 2016/0355760 A1    Dec. 8, 2016

(51) Int. Cl.

| | |
|---|---|
| C11D 3/39 | (2006.01) |
| C11D 1/14 | (2006.01) |
| C11D 3/36 | (2006.01) |
| C11D 3/20 | (2006.01) |
| C11D 3/43 | (2006.01) |
| C11D 3/34 | (2006.01) |
| C11D 1/24 | (2006.01) |
| A01N 25/02 | (2006.01) |
| A01N 25/30 | (2006.01) |
| A01N 25/22 | (2006.01) |
| A01N 59/00 | (2006.01) |

(52) U.S. Cl.
CPC .............. *C11D 3/394* (2013.01); *A01N 25/02* (2013.01); *A01N 25/22* (2013.01); *A01N 25/30* (2013.01); *A01N 59/00* (2013.01); *C11D 1/143* (2013.01); *C11D 1/24* (2013.01); *C11D 3/2034* (2013.01); *C11D 3/2068* (2013.01); *C11D 3/2093* (2013.01); *C11D 3/3409* (2013.01); *C11D 3/365* (2013.01); *C11D 3/3947* (2013.01); *C11D 3/43* (2013.01)

(58) Field of Classification Search
None
See application file for complete search history.

(56) References Cited

U.S. PATENT DOCUMENTS

| | | | |
|---|---|---|---|
| 4,070,442 A | 1/1978 | Watts | |
| 4,140,772 A | 2/1979 | Korenowski | |
| 4,812,173 A | 3/1989 | Tsao et al. | |
| 4,889,689 A | 12/1989 | Tsao | |
| 4,915,781 A | 4/1990 | Bohnen et al. | |
| 4,981,662 A | 1/1991 | Dougherty | |
| 5,846,570 A | 12/1998 | Barrow et al. | |
| 6,346,279 B1 * | 2/2002 | Rochon .................. | A01N 59/00 422/12 |
| 7,632,523 B2 | 12/2009 | Ramirez et al. | |
| 7,658,953 B2 | 2/2010 | Bobbert | |
| 8,021,609 B2 | 9/2011 | Doetsch et al. | |
| 8,246,906 B2 † | 8/2012 | Hei | |
| 8,357,356 B2 | 1/2013 | Zaeska et al. | |
| 8,802,613 B2 | 8/2014 | Bonislawski et al. | |
| 2002/0031556 A1 | 3/2002 | Lindahl | |
| 2003/0021853 A1 | 1/2003 | Wei et al. | |
| 2003/0087786 A1 | 5/2003 | Hei et al. | |
| 2003/0228996 A1 | 12/2003 | Hei et al. | |
| 2011/0182958 A1 | 7/2011 | Omidbakhsh | |
| 2012/0129755 A1 | 5/2012 | Zhu et al. | |
| 2012/0164236 A1 * | 6/2012 | Iwasa ..................... | A01N 59/16 424/616 |
| 2012/0230869 A1 | 9/2012 | Ramirez et al. | |
| 2013/0196890 A1 | 8/2013 | Post | |

FOREIGN PATENT DOCUMENTS

| | | |
|---|---|---|
| EP | 0092932 A1 | 11/1983 |
| EP | 0351772 A2 † | 1/1990 |
| WO | 03067989 A1 | 8/2003 |
| WO | 2011087786 A1 | 7/2011 |

OTHER PUBLICATIONS

"Dowfax Anionic Surfactants for High-Performance Products: The Right Choice in Formulations with Acids, Bleach, and Caustic", Dow Chemical Company, published Jul. 2000.*
"Introducing Rhodiasolv IRIS and Rhodiasolv Infinity", Rhodia, 2010.*
European Patent Office, European Search Report issued in corresponding European Patent Application No. 16172246.7-1375, dated Oct. 20, 2016, 9 pp.
AkzoNobel; Hydrogen Peroxide Product Information; URL: https://www.akzonobel.com/eka/system/images/AkzoNobel_hydrogen%20peroxide%20product%20information%20manual_December%202015_tcm56-94028.pdf (AkzoNobel) pH and Decomposition, pp. 8 (AkzoNobel, p. 8), (2015).†
Evonic Industries; Web Page: About Hydrogen Peroxide Stability & Decomposition. URL: http://h2o2.evonik.com/product/h2o2/en/about-hydrogen-peroxide/basic-information/stability-and-decomposition/pages/default.aspx (Evonik), (Accessed Mar. 10, 2017).†
Khalida Akhtar, Naila Khalid, Murad Ali; Effect of pH and Temperature on the Catalytic Properties of Manganese dioxide; Journal of The Chemical Society of Pakistan; vol. 34, No. 2, pp. 263; 2012. URL: http://jcsp.org.pk/ArticleUpload/4144-20045-1-CE.pdf (Akhtar et al.).†
Seymour S. Block, Disinfection, Sterilization, and Preservation (Lea and Febiger, Fourth Edition, Chapters 9 and 14: Peroxygen Compounds, pp. 167-180 (Block Chapter 9) and Surface-active Agents: Acid-Anionics Compounds, 256-261 (Block Chapter 14), (1991).†

* cited by examiner
† cited by third party

Primary Examiner — Bethany Barham
Assistant Examiner — Barbara Frazier
(74) Attorney, Agent, or Firm — Wood Herron & Evans LLP

(57) ABSTRACT

Stabilized hydrogen peroxide-containing compositions and methods of making same are disclosed. The compositions contain a stabilizer system made up of a disulfonate surfactant, a diester solvent, and a sulfonic acid or a salt thereof in a sufficient quantity to provide the stabilized hydrogen peroxide with an acidic pH value. The compositions are suitable for use as disinfectants, as cleaning agents, and in various personal care applications such as hair care and tooth whitening.

9 Claims, No Drawings

STABILIZED HYDROGEN PEROXIDE COMPOSITIONS AND METHOD OF MAKING SAME

TECHNICAL FIELD

The present invention is generally directed to stabilization of hydrogen peroxide containing compositions. In particular, the present invention is directed to stabilized hydrogen peroxide compositions and methods of making same.

BACKGROUND

Hydrogen peroxide solutions have been used for many years for a variety of purposes, including bleaching, disinfecting, and cleaning a variety of surfaces ranging from skin, hair, and mucous membranes to contact lenses to household and industrial surfaces and instruments. Unfortunately, unless stringent conditions are met, hydrogen peroxide solutions begin to decompose into $O_2$ gas and water within an extremely short time. Typical hydrogen peroxide solutions in use for these purposes are in the range of from about 0.5 to about 10% by weight of hydrogen peroxide in water. The rate at which such dilute hydrogen peroxide solutions decompose will, of course, be dependent upon such factors as pH and the presence of trace amounts of various metal impurities, such as copper or chromium, which may act to catalytically decompose the same. Moreover, at moderately elevated temperatures the rate of decomposition of such dilute aqueous hydrogen peroxide solutions is greatly accelerated. Hence, hydrogen peroxide solutions, which have been stabilized against peroxide breakdown, are in very great demand.

Stabilizers, which are usually sequestering agents, are normally added to hydrogen peroxide solutions to combat decomposition due to trace impurities, mainly dissolved metals. Many types of compounds have been used to fill this function, such as diols, quinones, stannate salts, pyrophosphates, various aromatic compounds and amino carboxylic acid salts. However, many of the previously suggested compounds have various issues and challenges associated with them, such as toxicity, environmental impact and poor performance.

Examples of specific compounds that have been suggested for use in solutions to protect against hydrogen peroxide decomposition include sodium phenolsulfate; sodium stannate; N,N-lower alkyl aniline, sulfamic acid, sulfolane, and di-straight chain lower alkyl sulfones and sulfoxides; phosphonic acids and their salts; acrylic acid polymers; polyphosphates; polyamino polyphosphonic acids and/or their salts; and specific combinations (or blends) of such compounds. However, in addition to toxicity and environmental impact concerns, many of these suggested compounds or blends have other drawbacks. For example, use of the specific stabilizer(s) either requires specific conditions to provide adequate hydrogen peroxide stability, such as specific pH levels, e.g., acidic conditions, or relatively low hydrogen peroxide concentrations, or has poor stability performance. The poor stability performance can either be poor stability performance generally or poor stability performance in specific formulations that contain other destabilizing components, e.g., surfactants.

Despite considerable efforts which have been applied with available stabilizer compounds to solve the problem, there still exists a need to provide hydrogen peroxide solutions which are highly stable without one or more of the aforementioned drawbacks and disadvantages.

SUMMARY

In accordance with an embodiment of the present invention, a stabilized hydrogen peroxide composition is provided that includes hydrogen peroxide; a disulfonate surfactant; a diester solvent; a sulfonic acid in a sufficient quantity to provide the stabilized hydrogen peroxide with an acidic pH value; and water.

In accordance with another embodiment of the present invention, a method of stabilizing a hydrogen peroxide containing composition in provided. The method includes combining an aqueous hydrogen peroxide solution with a stabilizing system comprising a disulfonate surfactant, a diester solvent, and a sulfonic acid in a sufficient quantity to provide the stabilized hydrogen peroxide with an acidic pH value.

DETAILED DESCRIPTION

In accordance with embodiments of the present invention, an aqueous solution of hydrogen peroxide is provided that demonstrates stability across a wide temperature range by the inclusion of a stabilizer system comprising a disulfonate surfactant, a diester solvent, and a sulfonic acid in a sufficient quantity to provide an acidic pH to the composition. The stabilized hydrogen peroxide compositions may further comprise additional ingredients, such as those described herein. In accordance with another embodiment, a method of stabilizing aqueous hydrogen peroxide compositions is further provided.

Hydrogen Peroxide ($H_2O_2$): In accordance with embodiments of the present invention, the stabilized hydrogen peroxide-containing compositions may comprise about 0.5 wt % hydrogen peroxide or more, wherein wt % is based on the total weight of the stabilized hydrogen peroxide composition. For example, the stabilized hydrogen peroxide compositions may comprise about 0.5 wt % to about 10 wt %, typically about 1 wt % to about 8 wt %, or about 2 wt % to about 7 wt %, or about 3 wt % to about 5 wt %, or about 4 to about 9 wt %, of hydrogen peroxide. The source of hydrogen peroxide is not particularly limited, and is conveniently commercially available. Typical industrial or food grade hydrogen peroxide solutions are provided as aqueous solutions having about 35 wt % to about 70 wt % hydrogen peroxide, and therefore may be diluted with water and/or other diluents (e.g., an alcohol) to achieve the desired final hydrogen peroxide concentration. The desired stability is imparted to the hydrogen peroxide composition by the stabilizer system that includes a disulfonate surfactant, a diester solvent, and a sulfonic acid, as further described below.

Disulfonate Surfactant: In accordance with embodiments of the present invention, the disulfonate surfactant is present in the stabilized hydrogen peroxide composition in an amount sufficient to provide the desired level of stability. For example, the disulfonate surfactant may be present in an amount in a range from about 0.1 wt % to about 10 wt %, wherein wt % is based on the total weight of the stabilized hydrogen peroxide composition. For example, the disulfonate surfactant may be present in the stabilized hydrogen peroxide composition in an amount of about 0.1 wt %, about 0.5 wt %, about 1 wt %, about 1.5 wt %, about 2 wt %, about 3 wt %, about 4 wt %, about 5 wt %, about 7 wt % or about 10 wt %, or in a range between any combination of these values. The disulfonate surfactant may include an alkyldiphenyloxide disulfonate compound or salt thereof. Exemplary salts include alkali metal or alkaline earth metal salts. The alkyldiphenyloxide disulfonate compounds are atypical surfactants and preferably include one or two alkyl chain groups of C6 to C20, linear and/or branched. Accordingly, exemplary alkyldiphenyloxide disulfonate compounds include, but are not limited to, C6 to C20 mono- and/or di-alkyldiphenyloxide disulfonate compounds. For example, the alkyl chains may be hexyl, heptyl, octyl, nonyl, decyl, undecyl, dodecyl, propadecyl, butadecyl, pentadecyl, hexadecyl, heptadecyl, octadecyl, nonadecyl, or didecyl. For example, Dowfax™ 8390, which is available from Dow Chemical Company, is a diphenyloxide disulfonate solution including disodium hexadecyl diphenyloxide disulfonate and dihexadecyl diphenyloxide disulfonate. Another exemplary alkyldiphenyloxide disulfonate compound solution is Dowfax™ 3B2, which is an n-decyl diphenyloxide disulfonate solution.

Diester Solvent: In accordance with embodiments of the present invention, the diester solvent is present in the stabilized hydrogen peroxide composition in an amount sufficient to provide the desired level of stability. For example, the diester solvent may be present in an amount in a range from about 0.1 wt % to about 10 wt %, wherein wt % is based on the total weight of the stabilized hydrogen peroxide composition. For example, the diester solvent may be present in the stabilized hydrogen peroxide composition in an amount of about 0.1 wt %, about 0.5 wt %, about 1 wt %, about 1.5 wt %, about 2 wt %, about 3 wt %, about 4 wt %, about 5 wt %, about 7 wt % or about 10 wt %, or in a range between any combination of these values. Exemplary diester solvents include, but are not limited to dialkyl methylglutarate, dialkyl adipate, dialkyl ethylsuccinate, dialkyl succinate, dialkyl glutarate and any combination thereof. The alkyl groups of the diester solvents may be the same or different and independently selected from methyl, ethyl, propyl, isopropyl, n-butyl, pentyl, isoamyl, hexyl, heptyl or octyl. In one embodiment, the diester solvent is dimethyl 2-methylglutarate, which is commercially available from Solvay Chemicals, Inc. as Rhodiasolv® Infinity.

Sulfonic Acid: In accordance with embodiments of the present invention, the stabilized hydrogen peroxide compositions contain a sufficient quantity of the sulfonic acid to provide the stabilized hydrogen peroxide with an acidic pH. Non-limiting examples of sulfonic acids include an aliphatic or aromatic hydrocarbon sulfonic acid, a halohydrocarbon sulfonic acid, or combinations thereof. Exemplary hydrocarbon sulfonic acids include C1 to C6 sulfonic acids, such as methane sulfonic acid, ethane sulfonic acid, propane sulfonic acid, butane sulfonic acid, pentane sulfonic acid, hexane sulfonic acid, or benzene sulfonic acid, or C7 to C10 sulfonic acids, such as toluene sulfonic acid, xylene sulfonic acid, or naphthalene sulfonic acid. In one embodiment, the sulfonic acid is methane sulfonic acid, which is commercially available from BASF as Lutropur® MSA.

Halohydrocarbon sulfonic acids are hydrocarbon sulfonic acids in which some or all of the hydrogen atoms on the hydrocarbon portion are replaced with a halogen, especially chlorine, bromine or fluorine. Exemplary halohydrocarbon sulfonic acids include fluoromethane sulfonic acid, difluoromethane sulfonic acid, trifluoromethane sulfonic acid, trichloroethane sulfonic acid, trichloromethane sulfonic acid. perchloroethane sulfonic acid, tribromomethane sulfonic acid, 3,3,3-tribromopropane sulfonic acid, tris(trifluoromethyl) methane sulfonic acid, and the like.

The sulfonic acid is present in the stabilized hydrogen peroxide composition in a sufficient quantity to provide an acidic pH (i.e., less than 7) at standard temperature and pressure (i.e., 25° C. and 1 atmosphere). For example, the pH of the stabilized hydrogen peroxide composition may be about 6.5 or less, about 6 or less, about 5.5 or less, about 5 or less, about 4.5 or less, about 4 or less, about 3.5 or less, about 3 or less, about 2.5 or less, about 2 or less, or about 1.5 or less, or in a range between any combination of these values. Accordingly, the pH of the stabilized composition may be in a range from about 6.5 to about 1, from about 3.5 to about 1.5, or from about 2.5 to about 1.5, for example.

In the event that it becomes necessary to add base (e.g., an excessive amount of sulfonic acid was introduced and the pH is lower than desired), then a base, such as aqueous sodium hydroxide or aqueous potassium hydroxide, may be added to the composition until the desired pH is attained. The base should be free from metal ions that would catalyze decomposition of hydrogen peroxide, such as ferrous ions, ferric ions, cupric ions, cuprous ions, manganous ions, and similar transition metal ions. The base should also be free from both organic and inorganic materials that would react with the hydrogen peroxide.

Water: After all the other ingredients have been accounted for, water comprises the balance of the hydrogen peroxide-containing composition. Because hydrogen peroxide is typically commercially available as a 30 wt % to 70 wt % aqueous solution, it is typically necessary to dilute the hydrogen peroxide with water or other diluent to obtain the desired hydrogen peroxide concentration. In accordance with an embodiment, the water or diluent may be free from metal ions that would catalyze decomposition of hydrogen peroxide, such as ferrous ions, ferric ions, cupric ions, cuprous ions, manganous ions, and similar transition metal ions. In accordance with another embodiment, the water or diluent may also be free from organic material that would be oxidized by hydrogen peroxide. In accordance with another embodiment, the water or diluent may also be free of inorganic materials that would react with hydrogen peroxide, such as chlorine ($Cl_2$), hypochlorous acid (HOCl), and sodium hypochlorite (NaOCl). Distilled or deionized water may be used.

Optional Ingredients: Additional ingredients may be included in the stabilized hydrogen peroxided composition, so long as the ingredients do not detrimentally affect the stability afforded by the stabilization system of the disulfonate surfactant, the diester solvent, and the sulfonic acid. Exemplary optional ingredients include an alcohol diluent, such as methanol, ethanol, propanol, butanol, pentanol, hexanol, and/or benzyl alcohol; a glycol ether; and/or an aliphatic phosphate ester.

The alcohol may be included in the stabilized hydrogen peroxide composition as a diluent or co-solvent. For example, when present, the alcohol may make up about 0.5 wt % to about 70 wt % of the stabilized hydrogen peroxide composition. In an embodiment, the stabilized hydrogen peroxide composition further includes about 30 wt % to about 60 wt % ethanol, for example, about 47 wt % SDA 23A, which is a denatured ethanol including acetone. In another embodiment, the stabilized hydrogen peroxide composition further includes about 5-20 wt % benzyl alcohol, for example, about 11 wt %. In another embodiment, the stabilized hydrogen peroxide composition further includes both ethanol and benzyl alcohol.

The glycol ether may be included in the stabilized hydrogen peroxide composition as a coalescent, a solubilizer, or as a viscosity reducer. The glycol ether, when present, may make up about 0.1 wt % to about 10 wt % of the stabilized hydrogen peroxide composition. For example, the glycol ether may be present in the stabilized hydrogen peroxide composition in an amount of about 0.1 wt %, about 0.5 wt %, about 1 wt %, about 1.5 wt %, about 2 wt %, about 3 wt %, about 4 wt %, about 5 wt %, about 7 wt % or about 10 wt %, or in a range between any combination of these values. The glycol ether may be selected from alkyl glycol ethers, such as diethylene glycol butyl ether (DGBE), ethylene glycol monomethyl ether ($CH_3OCH_2CH_2OH$), ethylene glycol monoethyl ether ($CH_3CH_2OCH_2CH_2OH$), ethylene glycol monopropyl ether ($CH_3CH_2CH_2OCH_2CH_2OH$), ethylene glycol monoisopropyl ether (($CH_3)_2CHOCH_2CH_2OH$), ethylene glycol monobutyl ether ($CH_3CH_2CH_2CH_2OCH_2CH_2OH$), ethylene glycol monophenyl ether ($C_6H_5CH_2OCH_2CH_2OH$), ethylene glycol monobenzyl ether ($C_6H_5OCH_2CH_2OH$), diethylene glycol monomethyl ether ($CH_3OCH_2CH_2OCH_2CH_2OH$), diethylene glycol monoethyl ether ($CH_3CH_2OCH_2CH_2OCH_2CH_2OH$), diethylene glycol mono-n-butyl ether ($CH_3CH_2CH_2CH_2OCH_2CH_2OCH_2CH_2OH$), propylene glycol phenyl ether ($C_6H_5CH_2OCH_2CH(CH_3)OH$), and/or any combination thereof. In one embodiment, the glycol ether is propylene glycol phenyl ether, which is commercially available from Dow Chemical Company as Dowanol™ PPh Glycol Ether solvent.

The aliphatic phosphate ester may be included in the stabilized hydrogen peroxide composition and may function as a hydrotrope or surfactant. When present, the aliphatic phosphate ester may be present in an amount from about 0.01 wt % to about 3 wt %, wherein wt % is based on the total weight of the stabilized hydrogen peroxide composition. For example, the aliphatic phosphate ester may be present in the stabilized hydrogen peroxide composition in an amount of about 0.01 wt %, about 0.02 wt %, about 0.03 wt %, about 0.04 wt %, about 0.05 wt %, about 0.08 wt %, about 0.1 wt %, about 0.5 wt %, about 1 wt %, about 2 wt %, or about 3 wt %, or in a range between any combination of these values. An exemplary aliphatic phosphate ester includes, but is not limited to, Multitrope™ 1214, which is commercially available from Croda, Inc.

In accordance with another embodiment, the stabilized hydrogen peroxide compositions may be free of sodium phenolsulfate; sodium stannate; N,N-lower alkyl aniline, sulfamic acid, sulfolane, mono and/or di-straight chain lower alkyl sulfones and sulfoxides; phosphonic acids and their salts; acrylic acid polymers; polyphosphates; polyamino polyphosphonic acids and/or their salts. In accordance with another embodiment, the stabilized hydrogen peroxide compositions may be free of any peroxycarboxylic acids, such as peroxyacetic acid.

In accordance with another embodiment, a method of stabilizing a hydrogen peroxide composition is provided. Stabilizing a hydrogen peroxide composition improves and/or maintains the effectiveness of the hydrogen peroxide composition, and is realized by formulating hydrogen peroxide with a disulfonate surfactant; a diester solvent; a sulfonic acid or a salt thereof in a sufficient quantity to provide the stabilized hydrogen peroxide with an acidic pH value; and water. In an embodiment, about 90% or more of the hydrogen peroxide present in the composition is stable for at least 12 months under normal room temperature (RT) storage conditions. In other embodiments, about 80% or more, or 70% or more, or 60% or more of the hydrogen peroxide present in the composition is stable for at least 12 months under normal room temperature storage conditions. Room temperature storage conditions for the hydrogen peroxide compositions are desirable in order to eliminate costly and inconvenient storage problems. While stability testing may be actually performed over a year, shelf stability may also be correlated to an abnormal or exaggerated storage condition for a predetermined amount of time to ensure a product's stability under normal storage conditions. One acceptable alternative in the hydrogen peroxide solution industry is to test stability at 54° C. for/over 14 days.

The stabilized hydrogen peroxide-containing compositions may be used in a variety of disinfectant, cleaning, personal care, pharmaceutical, textile and industrial applications. They disinfect the surfaces into which they are brought into contact and so can be used as disinfectant solutions or disinfectant lotions. When a surfactant is present, they both clean and disinfect the surfaces into which they are brought into contact. They can be applied by any method that insures good contact between the object to be cleaned and/or disinfected and the composition, such as spraying or wiping, and then removed by, for example, rinsing with water and/or wiping. The stabilized hydrogen peroxide-containing compositions may also be used, for example, as liquid detergents and in oral care applications, such as in tooth bleaching compositions. The stabilized hydrogen peroxide-containing compositions may also be applied on woven or nonwoven substrates for use as hydrogen peroxide wipes.

The advantageous properties of this invention can be observed by reference to the following examples, which illustrate but do not limit the invention.

EXAMPLES

TABLE 1

Ingredients used in examples.

| Ingredient | Chemical(s) | Source | Comment |
| --- | --- | --- | --- |
| Hydrogen Peroxide | Hydrogen peroxide | ACROS Organics | 35 wt % aq. solution |
| Disulfonate Surfactant | Disodium hexadecyl diphenyloxide disulfonate; Dihexadecyl diphenyloxide disulfonate | Dow Chemical Co. | DOWFAX ™ 8930 |
| Diester Solvent | Dimethyl 2-Methylglutarate + proprietary surfactants | Solvay | Rhodiasolv ® Infinity |
| Sulfonic Acid | Methane sulfonic acid | BASF | Lutropur ® MSA, ca. 70% |
| Ethanol | Ethanol; acetone | Lyondell Chemical Co. | SDA 23A |

TABLE 1-continued

Ingredients used in examples.

| Ingredient | Chemical(s) | Source | Comment |
|---|---|---|---|
| Benzyl Alcohol | Benzyl Alcohol | Alfa Aesar | 99% |
| Alkyl phosphate ester | Polyoxyethylene alkyl ether phosphate | Croda | Multitrope ™ 1214 |
| Glycol ether | Propylene glycol phenyl ether | Dow Chemical Co. | DOWANOL ™ PPh |

For Examples 1-4 shown in Table 2 (below), the order of addition of the ingredients to the mixing vessel are shown in parenthesis using upper case letters, where A is the first ingredient added to the mixing vessel.

Example 1

In one example, a stabilized hydrogen peroxide solution was prepared by sequentially adding Dowfax™ 8390, Rhodiasolv® Infinity, Multitrope™ 1214, 35% hydrogen peroxide, and Lutropur® MSA to a quantity of DI water while stirring. Hydrogen peroxide content was 8.23 wt % and solution pH was 1.76.

Example 2

In another example, a stabilized hydrogen peroxide solution was prepared by sequentially adding Dowfax™ 8390, Rhodiasolv® Infinity, 35% hydrogen peroxide, and Lutropur® MSA to a quantity of DI water while stirring. Hydrogen peroxide content was 8.18 wt % and solution pH was 1.77.

Example 3

In another example, a stabilized hydrogen peroxide solution was prepared by sequentially adding Dowfax™ 8390, Rhodiasolv® Infinity, 35% hydrogen peroxide, and Lutropur® MSA to a quantity of DI water while stirring. Hydrogen peroxide content was 1.63 wt % and pH was 1.72.

Example 4

In another example, a stabilized hydrogen peroxide solution was prepared by sequentially adding benzyl alcohol, Dowanol™ PPh, Rhodiasolv® Infinity, DI water, Lutropur® MSA, 35% hydrogen peroxide, and Dowfax™ 8390 to a quantity of SDA 23A ethanol. Hydrogen peroxide content was 1.63 wt % and solution pH was 2.50.

Control: A comparative sample was prepared by mixing DI water, citric acid, and hydrogen peroxide together. Hydrogen peroxide content was 1.7 wt % and pH of the solution was 1.87.

TABLE 2

Exemplary stabilized hydrogen peroxide compositions and comparative example.

| Ingredient | Ex-1 Wt % | Ex-2 Wt % | Ex-3 Wt % | Ex-4 Wt % | Control Wt % |
|---|---|---|---|---|---|
| DI water | 74.00 (A) | 74.00 (A) | 93.00 (A) | 27.00 (E) | 95.32 |
| Citric Acid | | | | | 3.48 |
| SDA23A | | | | 47.00 (A) | |
| Rhodiasolv ® Infinity | 1.00 (C) | 1.00 (C) | 1.00 (C) | 1.50 (D) | |
| Dowfax ™ 8390 | 1.10 (B) | 1.10 (B) | 1.10 (B) | 0.60 (H) | |
| Multitrope ™ 1214 | 0.05 (D) | | | | |
| Benzyl Alcohol | | | | 11.00 (B) | |
| DOWANOL ™ PPh | | | | 5.50 (C) | |
| Hydrogen Peroxide, 35% | 23.63 (E) | 23.63 (D) | 4.53 (D) | 4.50 (G) | 4.69 |
| Lutropur ® MSA 70% | 0.17 (F) | 0.16 (E) | 0.20 (E) | 0.10 (F) | |
| pH | 1.76 | 1.77 | 1.72 | 2.50 | 1.87 |
| HP content (%) | 8.23 | 8.18 | 1.63 | 1.63 | 1.7 |

| Stability: $H_2O_2$ % (pH) | | | | |
|---|---|---|---|---|
| (Batch I) | 10 days | 10 days | 9 days | 14 days |
| At RT | 8.33 | 8.30 | 1.47 | 1.53 |
| At 4° C. | 7.94 | 8.10 | 1.91 | n/a |
| At 60° C. (*55° C.) | 8.02 | 7.81 | 1.56 | 1.45* |

TABLE 2-continued

Exemplary stabilized hydrogen peroxide compositions and comparative example.

| (Batch II) | 17 days | 17 days | 17 days | 17 days | 17 days |
|---|---|---|---|---|---|
| At RT | 8.34 (1.60) | 8.33 (1.79) | 1.68 (1.85) | 1.68 (2.26) | 1.67 (1.86) |
| At 40° C. | 8.29 (1.66) | 8.14 (1.84) | 1.65 (1.86) | 1.67 (2.23) | n/a |
| At 55° C. | 8.28 (1.67) | 8.16 (1.83) | 1.63 (1.87) | 1.57 (2.31) | 0.98 (1.93) |
| (Batch I) | 15 months, 23 days | 15 months, 23 days | 2 months, 6 days | 11 months, 2 days | |
| At RT | 7.42 (1.74) | 7.76 (1.79) | 1.64 | 1.34 (2.44) | |

Stability testing: Values of hydrogen peroxide percentages (concentrations) disclosed herein were measured using the following method. The hydrogen peroxide-containing solutions were stored for the stated period of time (e.g., 17 days) and conditions. After the stated storage time period, the hydrogen peroxide concentration was measured using the redox titration method. The redox titration method is a standard method known in the art for measuring peroxide concentration. Specifically, the redox titration method was performed by weighing a 0.3 g sample to be tested into a 100 mL beaker using an analytical balance accurate to 0.001 g, and recording the weight. Then, 15 ml of refrigerated 10% $H_2SO_4$ was added, 5 drops of a Ferroin Indicator was added, and the initial volume of titrant was recorded. A 0.1 N Ceric Sulfate volumetric solution was then titrated, adding the titrant drop-wise until the Salmon color changed to yellow. (The yellow endpoint should be similar in color to the finished product solution.) No greater than 3 ml DI water was added as necessary to rinse the sides of the beaker where solution may have splashed. The final volume of titrant added for the solution was recorded, and then the hydrogen peroxide concentration was calculated as follows:

$$\% H_2O_2 = a \times N \times 1.7 / m$$

where: a=the net volume of ceric sulfate titrant consumed; N=the exact normality of ceric sulfate used; and m=the mass of the sample weighed. Hydrogen peroxide content was measured for samples stored at various temperatures over extended periods of time, as shown in Table 2.

When the storage period is long, the concentration of the hydrogen peroxide can alternatively be determined by measuring the concentration as described above after at least one hundred and twenty days and then extrapolating for the remainder of the period using first order kinetics, as is known in the art. The above-described method is performed just after manufacture of a peroxide product and at the end of the specified storage period in order to determine the absolute hydrogen peroxide concentrations as well as the percentage of the original concentration remaining, as is known in the art.

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope of the general inventive concept.

What is claimed is:

1. A stabilized hydrogen peroxide composition consisting of:
   hydrogen peroxide;
   a disulfonate surfactant;
   a diester solvent;
   a sulfonic acid in a sufficient quantity to provide the stabilized hydrogen peroxide with an acidic pH value;
   water; and
   optionally, one or a combination of an alcohol, a glycol ether, or an aliphatic phosphate ester.

2. The stabilized hydrogen peroxide composition of claim 1, wherein the sulfonic acid is present in a quantity to provide a pH value in a range from about 1.5 to about 2.5.

3. The stabilized hydrogen peroxide composition of claim 1, wherein the sulfonic acid is selected from the group consisting of a hydrocarbon sulfonic acid, a halohydrocarbon sulfonic acid, and combinations thereof.

4. The stabilized hydrogen peroxide composition of claim 1, wherein the optional alcohol is present and said alcohol is ethanol or benzyl alcohol, or both.

5. The stabilized hydrogen peroxide composition of claim 1, wherein the optional glycol ether is present.

6. The stabilized hydrogen peroxide composition of claim 1, wherein the optional aliphatic phosphate ester is present.

7. The stabilized hydrogen peroxide composition of claim 1, wherein the disulfonate surfactant includes an alkyldiphenyloxide disulfonate compound or a salt thereof.

8. The stabilized hydrogen peroxide composition of claim 1, wherein the hydrogen peroxide is present in the composition in an amount in a range from about 0.5 wt % to about 10 wt %, and the sulfonic acid is present in a quantity to provide a pH value of about 3.5 or less.

9. The stabilized hydrogen peroxide composition of claim 1, wherein at least one of the alcohol, the glycol ether, and the aliphatic phosphate ester is present.

* * * * *